United States Patent [19]

Parnoff

[11] Patent Number: 5,049,170
[45] Date of Patent: Sep. 17, 1991

[54] FILTER ASSEMBLY FOR GAS ANALYZER

[75] Inventor: George K. Parnoff, Walnut Creek, Calif.

[73] Assignee: Andros Incorporated, Berkeley, Calif.

[21] Appl. No.: 580,601

[22] Filed: Sep. 11, 1990

[51] Int. Cl.[5] .......................... B01D 46/02; B01D 39/14
[52] U.S. Cl. .......................................... 55/323; 55/333;
 55/428; 55/466; 55/498; 55/502
[58] Field of Search .................................. 55/318–323,
 55/333–336, 428, 466, 497, 498, 502, 275

[56] References Cited

U.S. PATENT DOCUMENTS

| | | | |
|---|---|---|---|
| Re. 32,989 | 7/1989 | Mann | 55/466 X |
| 1,825,031 | 9/1931 | Volk | 55/319 |
| 1,955,595 | 4/1934 | Morley | 55/322 |
| 3,364,658 | 1/1968 | Walker | 55/466 X |
| 3,527,027 | 9/1970 | Knight et al. | 55/275 |
| 3,559,764 | 2/1971 | Wheeler, Jr. | 55/466 X |
| 3,732,669 | 5/1973 | Chambers | 55/321 |
| 3,890,123 | 6/1975 | Kuga | 55/318 |
| 4,256,474 | 3/1981 | Berger, Jr. et al. | 55/318 X |
| 4,297,116 | 10/1981 | Cusick | 55/319 |
| 4,487,618 | 12/1984 | Mann | 55/323 |
| 4,848,989 | 7/1989 | Maeda | 55/319 |
| 4,865,815 | 9/1989 | Martin et al. | 55/318 X |
| 4,874,408 | 10/1989 | Overby | 55/466 X |

FOREIGN PATENT DOCUMENTS 660760  6/1938  Fed. Rep. of Germany ........ 55/318

Primary Examiner—Robert Spitzer
Attorney, Agent, or Firm—McCubbrey, Bartels, Meyer & Ward

[57] ABSTRACT

This invention is a filter assembly for preparing gases for an exhaust gas analyzer. A single housing includes at least three filter cavities, an inlet passage and two outlet passages. A coarse filter for filtering particulate matter and for condensate condensation is disposed in the first filter cavity. Condensate from the first cavity drains into the second filter cavity which has disposed therein a fine filter for filtering condensate. An outlet passage is connected to the second filter cavity for withdrawal of the condensate. A fine filter for filtering the exhaust gas is disposable in the third filter cavity which is coupled to the first filter cavity. A second outlet passage connects the third filter cavity to a pump for removal of the gas to be analyzed. The present invention thus provides a multiple filter assembly in a single housing with large fine filter area, minimal void volume, minimal interconnections, and convenient access to the individual filters. This achieves precise filtration of gases for analysis, allows low pump flow rates which save costs, lowers system stress, and reduces response time, minimizes leak potential, saves labor and equipment costs, and protects filters and peripheral equipment.

16 Claims, 4 Drawing Sheets

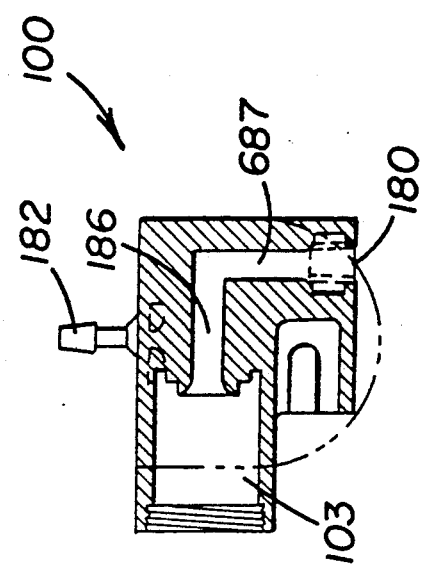
FIGURE 4
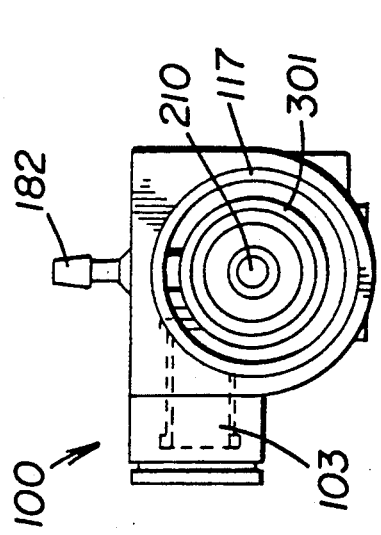
FIGURE 3
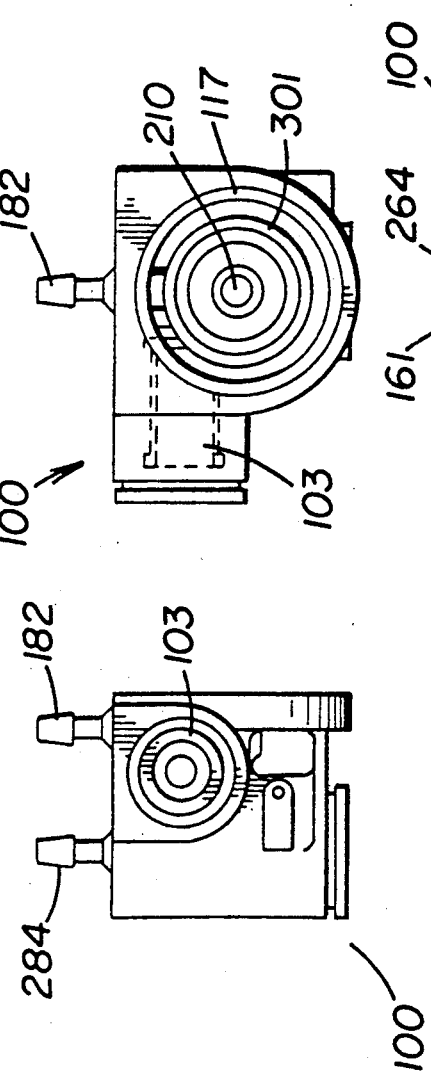
FIGURE 6
FIGURE 2
FIGURE 5
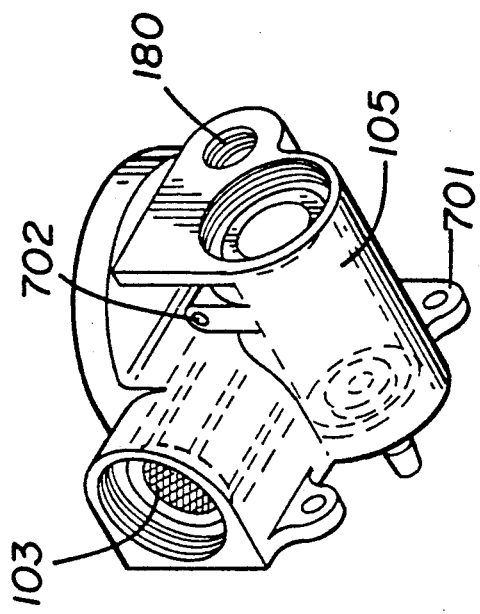
FIGURE 7

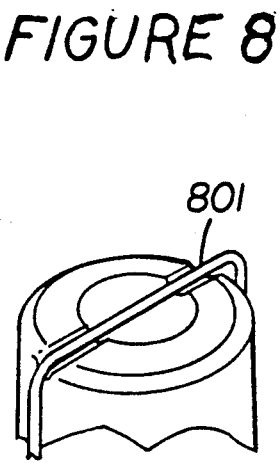
FIGURE 8A
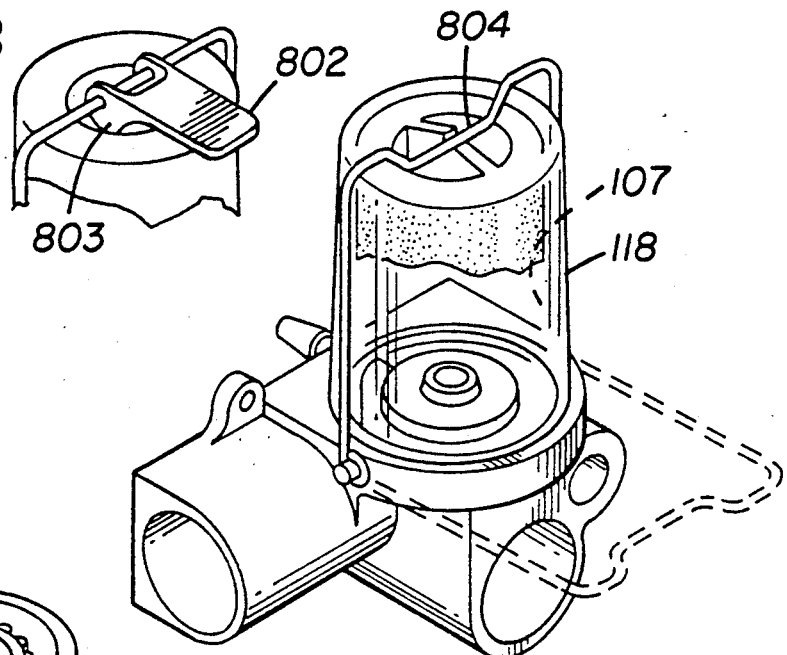
FIGURE 8B
FIGURE 8C
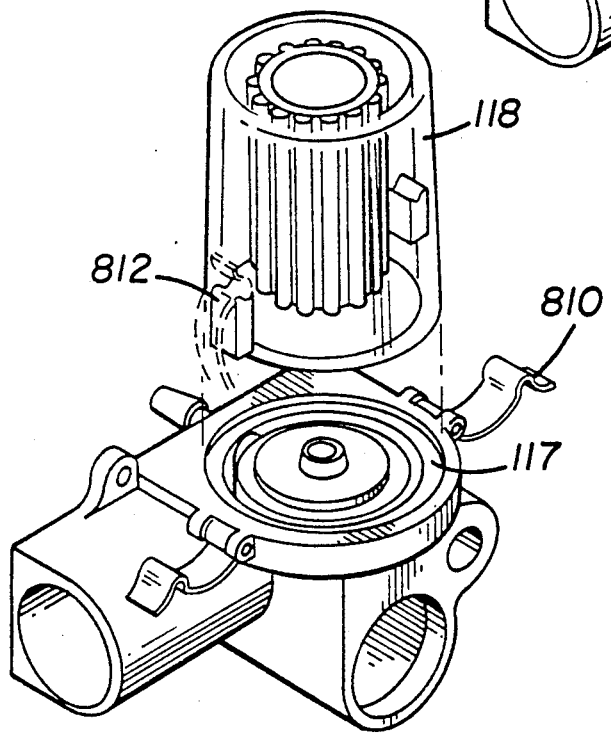
FIGURE 8D
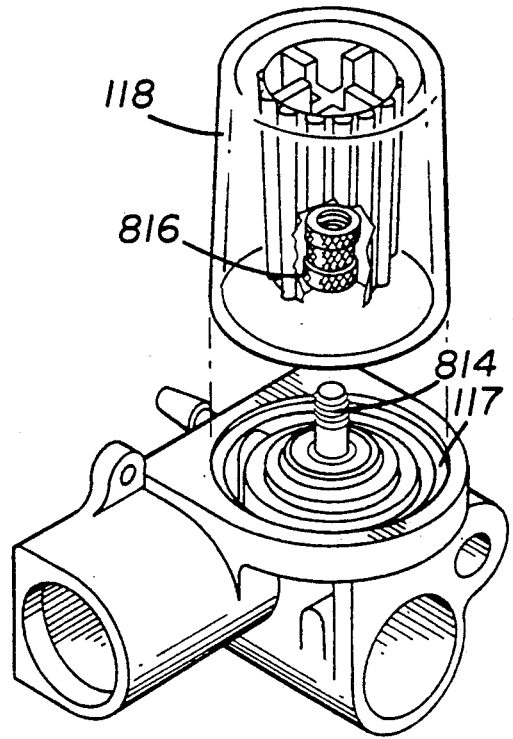
FIGURE 8E

FILTER ASSEMBLY FOR GAS ANALYZER

FIELD OF THE INVENTION

The present invention relates generally to the field of filter assemblies and more particularly to a multiple filter assembly for filtering gases while minimizing void volume and allowing convenient removal of filters.

BACKGROUND OF THE INVENTION

Gases for analysis may contain large and small particulate matter, condensates, and other contaminants as well as the constituents to be analyzed. For example, the exhaust gas of internal combustion engines is a highly complex mixture which must be filtered in order to allow analysis of constituents. Because of the wide variety of contaminants, several different types of filters are typically required to properly prepare a gas for analysis. Adding to the difficulties, contaminants such as particulate matter and condensates can harm filters, pumps, and the analyzer as well as cause operational inefficiencies. These inefficiencies include clogged filters, pump fouling, and void volumes resulting in high pump flow rate requirements.

Engine exhaust gases typically contain coarse and fine particulate matter, both liquid and vapor water, other condensates, and hydrocarbons, carbon monoxide, carbon dioxide, nitrogen oxides, oxygen, and other compounds to be analyzed. Contaminants must be filtered out by different type filters suited for the particular contaminant in order to accurately measure the constituents of the gas. The general filtration process involves first removing large particles, liquid water, and other condensates using a relatively coarse filter. The condensate is filtered by another finer filter before being drawn off by a pump. The filtered gas is then filtered for finer particles (typically less than 5 micron particles) by another filter assembly. In particular, the removal of all water traces before the final filter is important because water absorbs the hydrocarbons which is one of the gases to be analyzed. If water is present in the final fine filter, the hydrocarbon measurements will be inaccurate. Further, certain materials can absorb molecules to be analyzed. These absorption phenomena are termed "hydrocarbon hang-up" or "molecular hang-up." Thus, the filtration process is extremely important for accurate measurements of gas constituents and to protect the analyzer and pumps.

Typical prior art filtration devices utilized separate filter assemblies for each step in the filtration process. This required additional labor and time-consuming changes of devices. If the devices were connected, complicated interconnections of each unit would typically produce large void volumes. The void volumes necessitated high pump flow rates to move the gas through the filters and further significantly increased response times for the filter assembly in operation with an analyzer. The high pump rates also produce increased stress on system components.

Knight et al. U.S. Pat. No. 3,527,027 discloses a pressurized gas co-axial multifilter apparatus having cylindrical coarse and fine filters disposed concentrically about a common axis. At the bottom of the housing is a water bowl for trapping water. While Knight et al. performs the filtration functions in a single unit, it is not suitable for exhaust gases containing relatively large amounts of water. Exhaust gas condensate in a pressurized gas would soak the filters, rendering them inefficient and subject to hydrocarbon absorption. Because of Knight et al.'s co-axial configuration, the surface areas of the different filters are limited in size to that which fits concentrically in the apparatus. In particular for the final fine filter for exhaust gas analysis, it is preferable to use larger filters which are more efficient and last longer. If the surface area of Knight et al.'s fine filter is increased, a large void volume would be produced. This would then necessitate a high pump flow rate to move the gas through the system which would require more powerful pumps and greater costs. Because of the different substances and amounts to be filtered, the usable lifetimes of different filters are significantly different. Thus in maintaining the filters, it would be desirable to be able to remove each filter separately. To remove filters for replacement or cleaning in Knight et al.'s device requires opening the housing and removing of the entire internal assembly. That is, the removal of specific filters would be difficult because of their proximity and concentricity. Finally, exhaust gas analyzers typically operate by suction of exhaust gas into the analyzer rather than from compressed air injection as required in Knight et al.'s device.

SUMMARY OF THE INVENTION

Accordingly, it is a principal object of the present invention to provide a multiple filter assembly suitable for exhaust gas analysis in a single housing for convenience and efficiency of operation.

It is a further object of the present invention to maximize the fine filter area while minimizing void volume.

It is still a further object of the present invention to prevent liquid condensates from reaching the fine filter.

It is another object of the present invention to reduce the number of interconnections among filters to minimize the possibility of leaks in the system.

It is still another object of the present invention to provide a multiple filter assembly having convenient access to the different filters for cleaning and removal.

It is yet another object of the present invention to provide a multiple filter assembly which achieves filtration sufficient to protect certain filters therein from liquids and pumps connected thereto from particulates.

This invention is a filter assembly for preparing gases for an exhaust gas analyzer. A single housing includes at least three filter cavities, an inlet passage and two outlet passages. A coarse filter for filtering particulate matter and condensates is disposed in the first filter cavity. Condensate from the first cavity drains into the second filter cavity which has disposed therein a fine filter for filtering condensate. An outlet passage is connected to the second filter cavity for withdrawal of the condensate. A fine filter for filtering the exhaust gas is disposable in the third filter cavity which is coupled to the first filter cavity. A second outlet passage connects the third filter cavity to a pump for removal of the gas to be analyzed.

The present invention thus provides a multiple filter assembly in a single housing with large fine filter area, minimal void volume, minimal interconnections, and convenient access to the individual filters. This achieves precise filtration of gases for analysis, allows low pump flow rates which save costs, lowers system stress, and reduces response time, minimizes leak potential, saves labor and equipment costs, and protects certain of the filters from liquids and the peripheral equipment from particulates.

A further understanding of the nature and advantages of the present invention may be realized by reference to the Detailed Description of the Invention and the attached drawings.

BRIEF DESCRIPTION OF THE DRAWINGS

FIG. 2 is a cross-sectional side view of a mutually orthogonal configuration filter assembly according to the present invention.

FIG. 3 is a top plan view of a mutually orthogonal configuration filter assembly according to the present invention.

FIG. 4 is a side plan view of a mutually orthogonal configuration filter assembly showing gas outlet passage and liquid outlet passage and a cross-sectional view of a filter cavity according to the present invention.

FIG. 5 is a side plan view of assembly with cover removed according to the present invention.

FIG. 6 is a side cut-away view of filter assembly showing a passage from a filter cavity connected to an inlet passage for gas according to the present invention.

FIG. 7 is a bottom perspective view of a mutually orthogonal configuration filter assembly showing filter cavities, gas inlet passage, and securing means according to the present invention.

FIGS. 8A through 8E show various attaching means for securing a cover to the annular seat for a filter cavity according to the present invention.

DETAILED DESCRIPTION OF THE INVENTION

Figure 1:
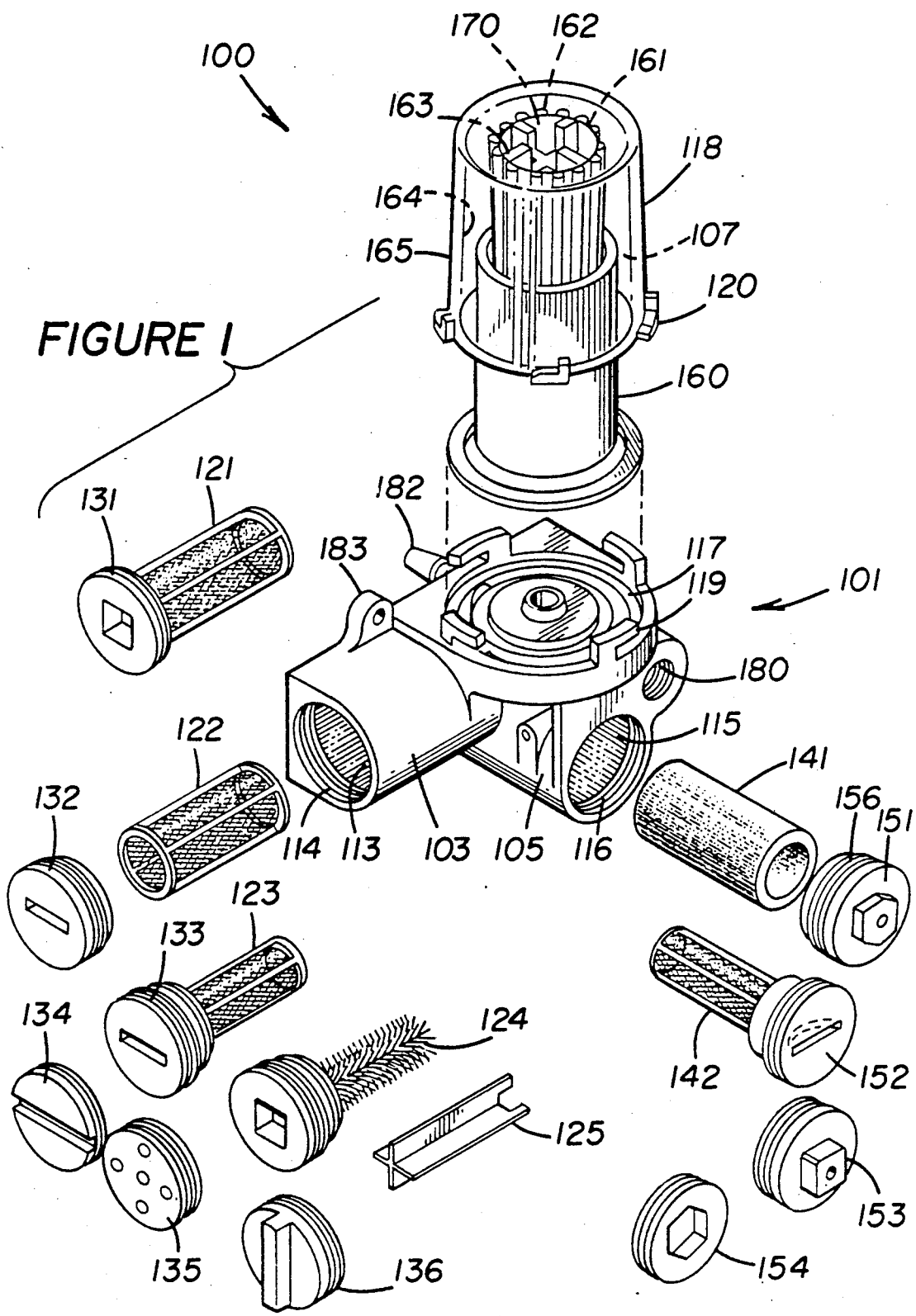
FIG. 1 is an exploded perspective view of a filter assembly in mutual orthogonal configuration and various filtration devices according to the present invention.

FIG. 1 is an exploded perspective view of an embodiment of the present invention showing an orthogonal configuration filter assembly 100 and various filtration devices which may be advantageously utilized therewith. A housing 101 has first, second, and third filter cavities 103, 105, and 107. In this embodiment, filter cavities 103 and 105 are substantially cylindrical and filter cavity 107 is substantially frusto-conical. It is understood that variations among cylindrical and frusto-conical shapes are within the scope of this invention. The cylindrical and frusto-conical axes in this embodiment are substantially mutually orthogonal, but variations from orthogonality are also within the scope of the invention. The axes of first filter cavity 103 and third filter cavity 107 intersect. The axes of second filter cavity 105 and third filter cavity 107 intersect, whereas the axis of first filter cavity 103 is offset from the axes of both filter cavities 105 and 107. Various other orientations of the three axes are also within the scope of the present invention, including non-orthogonal orientations.

Filter cavity 107 is formed from an annular seat 117 and cover 118. Cover 118 is secured to seat 117 by "L"-shaped hooking sleeves, of which 119 is representative, which engage "L"-shaped tabs, of which 120 is representative. Other securing means are described below. Cover 118 is frusto-conically shaped with a central surface 161, shown here with ribs 162 and supports 163, an inside surface 164, and an outside surface 165. A smooth central surface without ribs and/or supports can also be advantageously used. A filter 160, either frusto-conically or cylindrically shaped fits between inside surface 164 and central surface 161. Filter 160 is in this embodiment a fine filter made of borosilicate glass or other suitable material for the removal of fine particles, typically of twenty-five microns size or smaller. The annular shape of cover 118 with its central portion 170 minimizes void volume for filter 160 operation while maximizing the effective surface area of filter 160 for efficient filter operation.

Filter cavities 103 and 105 have apertures 113 and 115 respectively opening away from the center of housing 101. Representative filters for filter cavity 103 are shown at 121-123. These filters are typically coarse filters for removal of relatively large particulate matter and for water or other liquid condensations. Included are a nylon filter 121, a stainless steel filter 122, and various degrees of coarseness filters 123. Attachments such as a bristle cleaner 124 and a partition support 125 are also deployable within any of the cavities. Filters 121-125 fit into cavity 103 and are secured at the outwardly facing end by various caps 131-136 which are suitably designed for the individual filters 121-125 and for closing aperture 113. Further, caps 131-136 may be constructed with protrusions which will help to decrease void volume in the cavities. Aperture 113 in this embodiment has threads 114 so caps 131-136 also have threads for engagement into aperture 113. Any other suitable means of engagement such as simple plugs are within the scope of the invention. Filters 121-125 and caps 131-136 are advantageously designed to allow easy removal of filters from housing 101.

Representative filters for filter cavity 105 are shown as 141 and 142 for removing large and fine particulates from the condensate and drained to filter cavity 5. Filter 141 is a borosilicate glass filter and filter 142 is a stainless steel screen type filter. Various caps 151-154 are shown for securing filters 141 and 142 in filter cavity 105 and for closing aperture 115. Threads 116 are shown for engagement with representative threads 156 on cap 151. Again, any suitable means of securing and closing aperture 115 is within the scope of the invention.

It is understood that other kinds of filters in the broad sense of the word as something which selectively filters certain substances can be advantageously used in the filter cavities.

An inlet passage 180 for the gas to be analyzed to enter filter assembly 100 is in fluid communication with filter cavity 103. A gas outlet passage 182 is in fluid communication with filter cavity 107. Passages 180 and 182 are shown more clearly in FIG. 2. A flange-like attachment device 183 is shown for attachment of filter assembly 100 to a gas analyzer. However, any suitable attachment means may be employed for this purpose.

FIG. 2 is a cross-sectional side view of filter assembly 100 showing the particular advantages of operation of the present invention. Filter cavities 103, 105, and 107 are shown in mutually orthogonal configuration. Gas to be filtered enters at inlet passage 180, travels through passage 186 to filter cavity 103. A suitable coarse filter 228 filters large particles and condensates in the gas. The condensate drains to the bottom 288 of cavity 103 into filter cavity 105 where it is filtered for particulate matter by a suitable condensate filter 248. The draining is achieved by gravity and/or vacuum suction. The condensate is drawn off through outlet 284 which may be coupled to a pump (not shown) providing suction. Filter 248 thus protects the pump from fouling. The gas, now filtered of large particulates and condensate travels upwards through passage 285 into cavity 107 wherein a suitable filter 260 is disposed. Filter 260 filters fine particulate matter in the gas in final preparation for transmission to an analyzer (not shown) through passage 210 and out through outlet passage 182. Outlet passage 182 may be coupled to a pump to provide suction to pull the gas through the system. In one embodiment of the present invention, a single two-section pump is attached to both condensate outlet 284 and gas outlet 182 to provide suction for filter assembly 100.

FIG. 2 advantageously shows a central region 264 of cavity 107 having central surface 161. This configuration significantly decreases the void volume in cavity 107, thereby allowing lower pump flow rates, but also maximizes the effective surface area of filter 260 providing efficient filtration.

FIG. 3 is a top plan view of filter assembly 100. Annular seat 117 of filter cavity 107 is a series of concentric grooves 301 for seating of a filter and cover 118 (of FIG. 1). Filter cavity 103 is shown with its axis offset from the axis of annular seat 117. Gas outlet passage 182 is in fluid communication, shown as dashed lines, with passage 210. Suitable sealing gaskets (not shown) may be advantageously disposed on annular seat 117 to seal cavity 107.

FIG. 4 is a side plan view of filter assembly 100 showing gas outlet passage 182 and condensate outlet passage 284 and a cross-sectional view of filter cavity 103.

FIG. 5 is a side plan view of filter assembly 100 with cover 118 removed and showing filter cavity 105 in cross-section, filter cavity 103 in side view, inlet passage 180, and annular seat 117.

FIG. 6 is a side cut-away view of filter assembly 100 showing passage 186 from filter cavity 103 connected through passage 687 to inlet passage 180.

FIG. 7 is a bottom perspective view of filter assembly 100 showing filter cavities 103 and 105, gas inlet passage 180, and securing means 701 and 702.

FIGS. 8A-8E show various attaching means for securing cover 118 to annular seat 117. FIG. 8A shows a spring wire latch 801. FIG. 8B shows spring wire latch 801 with a latch tab 802 having a distended portion 803 for providing additional pressure on cover 118. FIG. 8C shows a spring wire latch having an indented portion 804. FIG. 8D shows a distributor cap type arrangement having spring tabs 810 securable to tab seats 812. FIG. 8E shows a screw-on arrangement having a bolt 814 disposed on annular seat 117 and a corresponding nut 816 secured to cover 118 for threadable engagement with bolt 814. Additionally, cover 118 can be secured by threadable engagement to annular seat 117 by means of corresponding threads in cover 118 and annular seat 117, or by screws around the periphery of cover 118. It is understood that any suitable securing means for attaching and holding cover 118 to seat 117 is within the scope of the invention.

Figure 9:
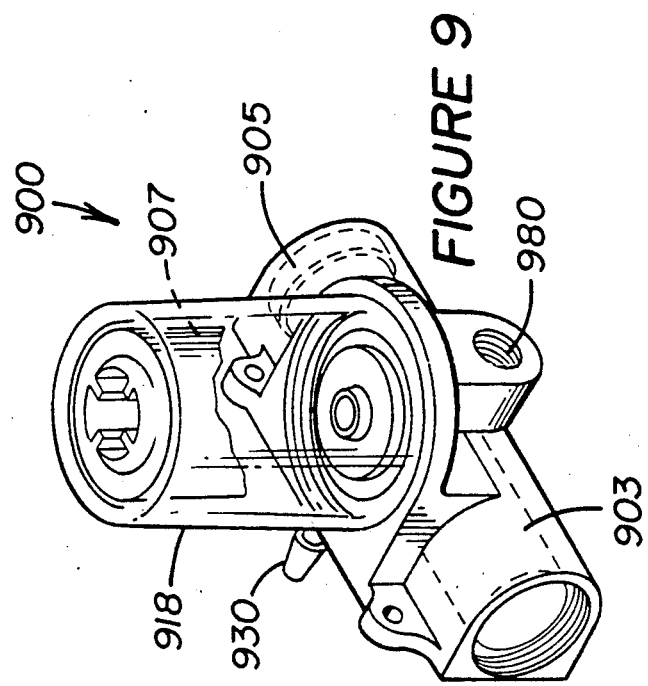
FIG. 9 is a perspective view of an alternate embodiment of an axially co-linear configured filter assembly according to the present invention.
Figure 10:
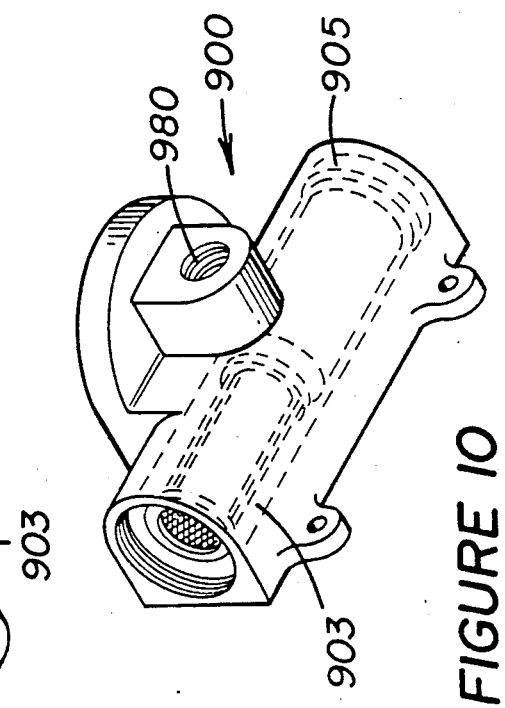
FIG. 10 is a bottom perspective view of the axially co-linear configuration of a filter assembly with cover removed according to the present invention.

FIG. 9 is a perspective view of an alternate embodiment of a filter assembly 900 according to the present invention wherein the first and second filter cavities are axially co-linear in configuration. Filter cavity 903, typically for supporting a coarse filter, is substantially cylindrical with an axis substantially co-linear with the axis of filter cavity 905, typically for supporting a condensate filter. Filter cavity 907 and gas inlet passage 980 are in relative configuration substantially similar to the embodiment described above. FIG. 10 is a bottom perspective view of the axially co-linear configuration of filter assembly 900 with cover 918 removed.

Figure 11:
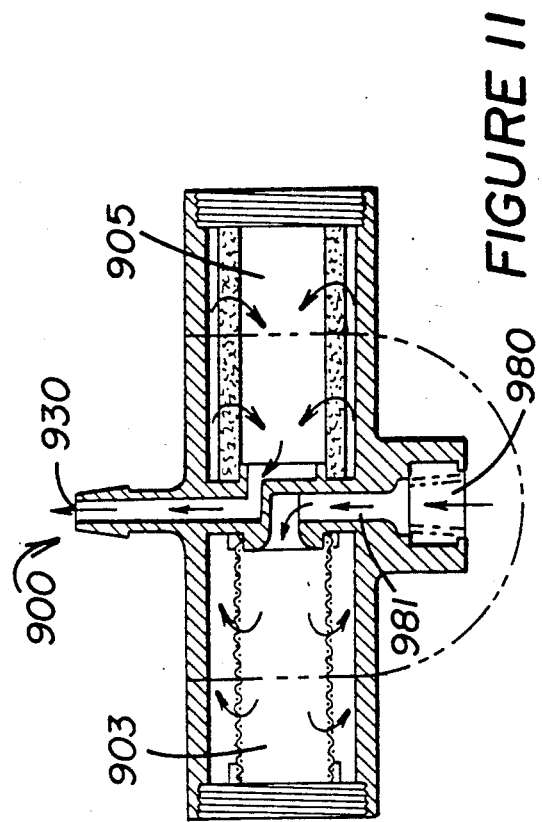
FIG. 11 is a side cross-sectional view of the axially co-linear configuration of a filter assembly showing a passage in fluid communication with a coarse filter cavity according to the present invention.
Figure 12:
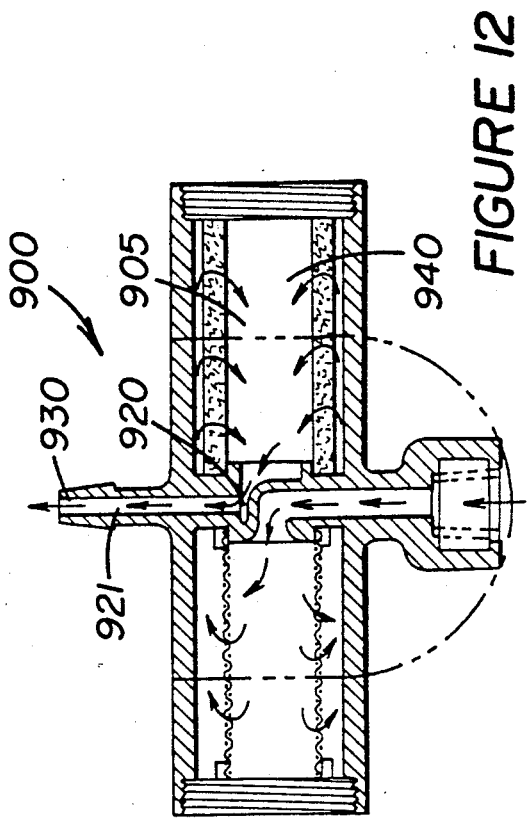
FIG. 12 is a side cross-sectional view showing the flow of water or other liquid through a liquid filter cavity according to the axially co-linear embodiment of the present invention.

FIG. 11 is a side cross-sectional view of filter assembly 900 showing passage 981 in fluid communication with filter cavity 903. Gas is filtered for large particulates and condensate in filter cavity 903. Condensate drains to the bottom of cavity 903 and is forced by vacuum suction into cavity 905. Filter cavity 903 is in fluid communication with filter cavity 107 in substantially the same manner as the embodiment described above. FIG. 12 is a side cross-sectional view showing the flow of liquid through a filter 940, through passage 920, and passage 921, to outlet passage 930, which may be advantageously connected to a pump (not shown) providing the vacuum suction.

The housings and filters of the present invention are constructed of materials which are impervious to molecular absorption of the molecules of the gases to be analyzed. This is to avoid molecular or hydrocarbon hang-up. For example, to avoid hydrocarbon hang-up, the filters can be constructed of borosilicate glass, Teflon, or stainless steel, and the housing can be constructed of stainless steel or some other suitable metal or polycarbonate plastic.

While the above description provides a full and complete description of the preferred embodiments of the present invention, various modifications, alternate constructions, and equivalents may be employed while still remaining within the scope of the invention. For example, although the description is with reference to the filtration of exhaust gases, it could be applied to any contaminated gases such as from furnaces, combustion reactions of all kinds, naturally occurring gases, and the like. Further, liquids other than water or other condensate may be advantageously removed by the filter assembly of the present invention. Therefore, the above description and illustrations should not be construed as limiting the scope of the invention which is defined by the following claims.

What is claimed is:

1. A filter assembly for a gas analyzer comprising:
    a housing including first, second, and third filter cavities, a first inlet passage and first and second outlet passages;
    said first inlet passage being in fluid communication with said first filter cavity and further having means for connection to a source of gas;
    said first filter cavity having means for supporting therein a substantially coarse filter for filtering particulate matter and for separating liquids;
    said second filter cavity having means for supporting therein a substantially fine liquids filter for filtering liquids;

said second filter cavity being operatively positioned with respect to said first filter cavity to drain, by gravity, liquid from said first filter cavity;

said first outlet passage providing fluid communication from said second filter cavity for removal of liquid therefrom;

said third filter cavity having means for supporting therein a substantially fine gas filter for filtering the gas;

said third filter cavity being operatively positioned with respect to said first filter cavity to receive gases filtered therefrom; and said second outlet passage being in fluid communication with said third filter cavity and having means for connection to a pump for removal of filtered gas therefrom.

2. The filter assembly of claim 1 wherein said gas is exhaust gas.

3. The filter assembly of claim 1 wherein said liquid is water.

4. The filter assembly of claim 1 wherein said housing and said filter cavities are shaped so as to minimize void volume in said filter cavities and passages.

5. The filter assembly of claim 1 wherein said third filter cavity is substantially frusto-conically shaped having an inner and outer surface defining an internal, substantially frusto-conically shaped region for disposal of said substantially fine gas filter; and wherein said fine gas filter has a substantially cylindrical shape having inner and outer surfaces.

6. The filter assembly of claim 1 wherein said housing and said filters are constructed from materials being impervious to molecular absorption of gases to be analyzed.

7. The filter assembly of claim 1 wherein said housing has first, second, and third apertures therein in connection with said first, second, and third filter cavities for removal of said filters from said filter cavities.

8. The filter assembly of claim 7 wherein said apertures in said housing are engaged by first, second, and third caps for closing said apertures and for providing protrusions into said cavity for decreasing void volume therein.

9. The filter assembly of claim 8 wherein said third cap is frusto-conically shaped and includes attachment means for securing said third cap over said third aperture.

10. The filter assembly of claim 1 wherein said filter cavities are substantially cylindrical in shape having first, second, and third cylindrical axes, said axes being mutually orthogonal.

11. The filter assembly of claim 1 wherein said filter cavities are substantially frusto-conical in shape having first, second, and third conic axes, said axes being mutually orthogonal.

12. The filter assembly of claim 1 wherein said first and second filter cavities are substantially cylindrical in shape having first and second cylindrical axes, said axes being substantially co-linear.

13. The filter assembly of claim 12 wherein said third filter cavity is substantially frusto-conical in shape having a conic axis being substantially orthogonal to said axes of said first and second cavities.

14. The filter assembly of claim 1 wherein said housing has a substantially planar surface for flush attachment to a gas analyzer and means for securing said housing to the gas analyzer.

15. The filter assembly of claim 1 further comprising pump means, coupled to said first and second outlet passages, for providing suction for said filter assembly through both outlet passages.

16. A filter assembly for an exhaust gas analyzer comprising:

a housing including first, second, and third filter cavities, a first inlet passage and first and second outlet passages;

said first inlet passage being in fluid communication with said first filter cavity and further having means for connection to a source of exhaust gas;

said first filter cavity having means for supporting therein a substantially coarse filter for filtering particulate matter and for separating liquids;

said second filter cavity having means for supporting therein a substantially fine liquids filter for filtering liquids;

said second filter cavity being operatively positioned with respect to said first filter cavity to drain liquid from said first filter cavity;

said first outlet passage providing fluid communication from said second filter cavity for removal of condensate therefrom;

said third filter cavity having means for supporting therein a substantially fine gas filter for filtering the exhaust gas;

said third filter cavity being operatively positioned with respect to said first filter cavity to receive gases filtered therefrom;

said second outlet passage being in fluid communication with said third filter cavity and having means for connection to a pump for removal of filtered gas therefrom;

said filter cavities further being shaped so as to minimize void volume in said filter cavities and passages;

said third filter cavity further being substantially frusto-conically shaped having an inner and outer surface defining an internal, substantially frusto-conically shaped region for disposal of said substantially fine gas filter, and said housing further having first, second, and third apertures therein in connection with said first, second, and third filter cavities for removal of said filters from said filter cavities.

* * * * *